United States Patent [19]

Fujita

[11] Patent Number: 5,023,802
[45] Date of Patent: Jun. 11, 1991

[54] METHOD FOR PROCESSING INFORMATION ON CHEMICAL REACTIONS

[75] Inventor: Shinsaku Fujita, Minami-ashigara, Japan

[73] Assignee: Fuji Photo Film Co., Ltd., Kanagawa, Japan

[21] Appl. No.: 311,386

[22] Filed: Feb. 15, 1989

Related U.S. Application Data

[63] Continuation of Ser. No. 905,658, Sep. 11, 1986, abandoned.

[30] Foreign Application Priority Data

Sep. 13, 1985 [JP] Japan .................................. 60-203690

[51] Int. Cl.$^5$ .............................................. G06F 15/20
[52] U.S. Cl. .................................................. 364;496
[58] Field of Search ............... 364/496, 497, 200, 498, 364/900

[56] References Cited

U.S. PATENT DOCUMENTS

| | | | |
|---|---|---|---|
| 4,085,443 | 4/1978 | Dubois et al. | 364/900 |
| 4,205,391 | 5/1980 | Ulyanor et al. | 364/496 |
| 4,365,303 | 12/1982 | Hannah et al. | 364/498 |
| 4,473,890 | 9/1984 | Araki | 364/900 |
| 4,642,762 | 2/1987 | Fisanick | 364/300 |
| 4,747,059 | 5/1988 | Hirayama et al. | 364/900 |

OTHER PUBLICATIONS

Barnard et al., "Computer Storage and Retrieval of Generic Structures in Chemical Patents, 4; An Extended Connection Table Representation for Generic Structure," 4/5/82, pp. 160–164.
Krishnamurthy, "Wisehom; A Furmal Organic Chemical Nomenclature System," 4/28/81; pp. 152–159.
Skolnik, "A Multilingual Index via the Multiterm System," 2/16/71; pp. 128–133.

Primary Examiner—Joseph L. Dixon
Assistant Examiner—Ellis B. Ramirez
Attorney, Agent, or Firm—Sixbey, Friedman, Leedom & Ferguson

[57] ABSTRACT

There is disclosed a method for processing information on a two or more-step chemical reaction wherein individual reactions of producing at least one product from at least one starting material take place consecutively, information on the reactions at individual steps being given as bond information in which bonds linking two nodes are distinguished between the starting material and the product topologically superposed thereon and denoted by a pair of integers ($a_x{}^i$, $b_x{}^i$), wherein the integer $a_x{}^i$ is bond multiplicity of the bond x of the starting material in the i-th step reaction and the integer $b_x{}^i$ is difference in the bond multiplicity of the bond x between the product and the starting material in the i-th step reaction, which comprises performing the following operation on the basis of said bond information:

$$a_x{}^{jk} = a_x{}^j$$

$$b_x{}^{jk} = b_x{}^j + b_x{}^{j+1} + \ldots + b_x{}^{k-1} + b_x{}^k$$

wherein the integer $a_x{}^{jk}$ is bond multiplicity of the bond x of the starting material in the consecutive reactions of from the j-th step to the k-th step and the integer $b_x{}^{jk}$ is difference in the bond multiplicity of the bond x between the product and the starting material in the consecutive reactions, to obtain information on the consecutive reactions as bond information denote by a pair of integers ($a_x{}^{jk}$, $b_x{}^{jk}$).

4 Claims, 2 Drawing Sheets

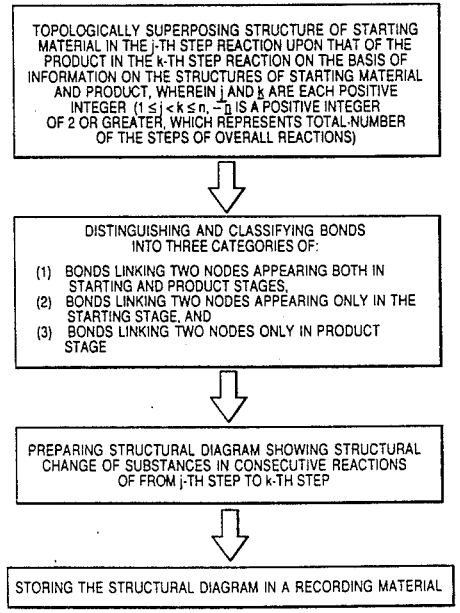

TOPOLOGICALLY SUPERPOSING STRUCTURE OF STARTING MATERIAL IN THE j-TH STEP REACTION UPON THAT OF THE PRODUCT IN THE k-TH STEP REACTION ON THE BASIS OF INFORMATION ON THE STRUCTURES OF STARTING MATERIAL AND PRODUCT, WHEREIN $j$ AND $k$ ARE EACH POSITIVE INTEGER ($1 \leq j < k \leq n$, $n$ IS A POSITIVE INTEGER OF 2 OR GREATER, WHICH REPRESENTS TOTAL NUMBER OF THE STEPS OF OVERALL REACTIONS)

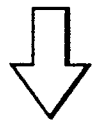

DISTINGUISHING AND CLASSIFYING BONDS INTO THREE CATEGORIES OF:

(1) BONDS LINKING TWO NODES APPEARING BOTH IN STARTING AND PRODUCT STAGES,
(2) BONDS LINKING TWO NODES APPEARING ONLY IN THE STARTING STAGE, AND
(3) BONDS LINKING TWO NODES ONLY IN PRODUCT STAGE

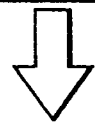

PREPARING STRUCTURAL DIAGRAM SHOWING STRUCTURAL CHANGE OF SUBSTANCES IN CONSECUTIVE REACTIONS OF FROM j-TH STEP TO k-TH STEP

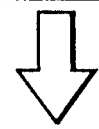

STORING THE STRUCTURAL DIAGRAM IN A RECORDING MATERIAL

*FIG. 1*

TOPOLOGICALLY SUPERPOSING STRUCTURE OF STARTING MATERIAL IN THE j-TH STEP REACTION UPON THAT OF THE PRODUCT IN THE k-TH STEP REACTION ON THE BASIS OF INFORMATION ON THE STRUCTURES OF STARTING MATERIAL AND PRODUCT, WHEREIN j AND k ARE EACH POSITIVE INTEGER ($1 \leq j < k \leq n$, -- n IS A POSITIVE INTEGER OF 2 OR GREATER, WHICH REPRESENTS TOTAL NUMBER OF THE STEPS OF OVERALL REACTIONS)

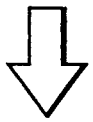

DISTINGUISHING AND CLASSIFYING BONDS INTO THREE CATEGORIES OF:

(1) BONDS LINKING TWO NODES APPEARING BOTH IN STARTING AND PRODUCT STAGES,
(2) BONDS LINKING TWO NODES APPEARING ONLY IN THE STARTING STAGE, AND
(3) BONDS LINKING TWO NODES ONLY IN PRODUCT STAGE

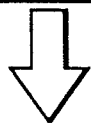

PREPARING A CONNECTION TABLE CONTAINING INFORMATION ON NODES, NEIGHBORING NODES AND BONDS LINKING THE TWO NODES WITH RESPECT TO THE CONSECUTIVE REACTIONS OF FROM j-TH STEP TO k-TH STEP

STORING THE CONNECTION TABLE IN A RECORDING MATERIAL

*FIG. 2*

METHOD FOR PROCESSING INFORMATION ON CHEMICAL REACTIONS

This application is a continuation of Ser. No. 06/905,658, filed 9/11/86, now abandoned.

BACKGROUNDS OF THE INVENTION

1. Field of the Invention

The present invention relates to a method for processing information on chemical reactions and more particularly, to a method for processing information on changes in the chemical structures of substances concerned with chemical reactions.

2. Description of the Prior Art

Various methods for recording structural information on chemical substances, particularly organic compounds have been proposed and attempted with the development of computers in recent years. A vast amount of organic compounds and organic reactions have been studied and worked out up to the present, and it is highly required that known chemical substances or chemical reactions are retrieved in a short time, or methods for the synthesis of new substances having the desired properties are found out, by effectively utilizing information on said known compounds and reactions. For this purpose, development of a new representation mode for chemical substances and chemical reactions is needed, which can be processed by computer (that is, which can be logically judged by computer) instead of an ordinary mode such as structural formula which can be readily treated by chemists.

Typical methods for recording chemical substances (methods for the representation or description of chemical substances) are a linear notation method such as WLN (Wiswesser Linear Notation) and a method using connection table. These methods are described in, for example, W. T. Wipke, S. R. Heller, R. J. Feldmann and E. Hyde (Eds.): "Computer Representation and Manipulation of Chemical Information", John Wiley and Sons, New York, 1974. The connection table is a list in which the kind of atoms and the kinds of neighbor atoms and bonds, etc. appeared in the structural formula of chemical substance are tabulated and the connection table has an advantage that chemical substances can be retrieved atom by atom as compared with the linear notation.

Further, methods for recording information on change in the chemical structures of substances (on chemical reactions) have been proposed, but a satisfactory representation method is not developed as yet. For instance, as methods for the description of chemical reactions, there are methods using a reaction code, such as a method described in J. Valls and O. Scheiner: "Chemical Information Systems", ed. by E. Ash and E. Hyde, Ellis Horwood Limited, 1975, p. 231-248; a method described in M. A. Lobeck, Angew. Chem. Intern. Ed. Engl., 9, 578(1970); and a method described in H. J. Ziegler, J. Chem. Inf. Comput. Sci., 19, 141(1979). In these methods, a view of the representation for chemical reactions is fixed and hence, these methods have a disadvantage that any novel chemical reactions can not be described. Further, there are disadvantages that since structural information on chemical substances and information on structural changes thereof are recorded in a separate form, it is hard to make an effective information retrieval.

There are other known recording methods worked out for design of synthetic pathways of chemical substances, for instance, methods described in E. J. Corey, R. D. Cramer and W. J. Howe, J. Am. Chem. Soc., 94, 440(1972); and I. Ugi, J. Bauer, J. Braodt, J. Friedrich, J. Gasteiger, L. Jochum and W. Schubert, Angew. Chem. Intern. Ed. Engl., 18, 111(1979).

SUMMARY OF THE INVENTION

It is an object of the present invention to provide a novel processing method for recording and storing information on structural changes of substances in consecutive chemical reactions.

It is another object of the present invention to provide a processing method for recording and storing integrated information on consecutive chemical reactions including information on starting materials, products and structural changes therebetween in a new representation mode which can be processed by computer.

The present invention provides:

[1] a method for processing information on a two or more-step chemical reaction wherein individual reactions of producing at least one product from at least one starting material take place consecutively, to record and store said information, which comprises:

topologically superposing structure of the starting material in the j-th step reaction upon that of the product in the k-th step reaction on the basis of information on the structures of the starting material and the product, wherein j and k are each a positive integer satisfying the condition of $1 \leq j < k \leq n$ and n is a positive integer of 2 or greater, being the total number of steps of the overall reaction;

distinguishing and classifying bonds into three categories of (1) bonds linking two nodes appearing both in the starting and product stages, (2) bonds linking two nodes appearing only in the starting stage and (3) bonds linking two nodes only in the product stage; and preparing a structural diagram showing structural change of substances in the consecutive reactions of from the j-th step to the k-th step, and

[2] a method for processing information on a two or more-step chemical reaction wherein individual reactions of producing at least one product from at least one starting material take place consecutively, to record and store said information, which comprises:

topologically superposing structure of the starting material in the j-th step reaction upon that of the product in the k-th step reaction on the basis of information on the structures of the starting material and the product, wherein j and k are each a positive integer satisfying the condition of $1 \leq j < k \leq n$ and n is a positive integer of 2 or greater, being the total number of steps of the overall reaction;

distinguishing and classifying bonds into three categories of (1) bonds linking two nodes appearing both in the starting and product stages, (2) bonds linking two nodes appearing only in the starting stage and (3) bonds linking two nodes only in the product stage; and preparing a connection table containing information on nodes, neighboring nodes and bonds linking said two nodes with respect to the consecutive reactions of from the j-th step to the k-th step.

It is a further object of the present invention to provide a novel processing method for obtaining integrated information on consecutive chemical reactions on the basis of information on individual reactions.

It is a still further object of the present invention to provide a processing method for recording and storing integrated information on consecutive chemical reactions on the basis of information on individual reactions in a new representation mode which can be processed by computer.

The present invention also provides a method for processing information on a two or more-step chemical reaction wherein individual reactions of producing at least one product from at least one starting material take place consecutively, said information on the reactions at individual steps being given as bond information in which bonds linking two nodes are distinguished between the starting material and the product topologically superposed thereon and denoted by a pair of integers $(a_x^i, b_x^i)$, wherein i is a positive integer satisfying the condition of $1 \leq i \leq n$, n is a positive integer of 2 or greater, being the toal number of steps of the overall reaction, the integer $a_x^i$ is bond multiplicity of the bond x of the starting material in the i-th step reaction and the integer $b_x^i$ is difference in the bond multiplicity of the bond x between the product and the starting material in the i-th step reaction, which comprises performing the following operation for said bond information:

$$a_x^{jk} = a_x^j$$

$$b_x^{jk} = b_x^j + b_x^{j+1} + \ldots + b_x^{k-1} + b_x^k$$

wherein j and k are each a positive integer satisfying the condition of $1 \leq j < k \leq n$, the integer $a_x^{jk}$ is bond multiplicity of the bond x of the starting material in the consecutive reactions of from the j-th step to the k-th step and the integer $b_x^{jk}$ is difference in the bond multiplicity of the bond x between the product and the starting material in said consecutive reactions;

whereby information on the consecutive reactions of from the j-th step to the k-th step is obtained as bond information in which bonds linking two nodes are denoted by a pair of integers $(a_x^{jk}, b_x^{jk})$.

In the first aspect of the present invention, information on a plurality of consecutive reactions (multi-step reaction) can be integrated on the basis of the inputted information on each of starting materials and products concerned with said multi-step reaction and obtained automatically in the form of a two-dimensional or three-dimensional structural diagram (graph) and/or a connection table according thereto. The term "structural diagram (graph)" used herein means a diagram (referred to as "imaginary transition structure") which represents the changes in the chemical structures of substances related to a given chemical reaction in such a representation mode that bonds linking two nodes in the reaction system are distinguished and classified into three categories of (1) bonds linking two nodes appearing in the starting stage, (2) bonds linking two nodes appearing only in the product stage and (3) bonds linking two nodes appearing both in the starting and product stages. By using this structural diagram, the chemical reaction can be described by a form which is visually acceptable and readily comprehensible to chemists and technologists in accordance with ordinary structural formula of chemical substance or the three-dimensional form thereof. The connection table according to said structural diagram is a table which essentially consists of a combination of the kind of nodes and the kinds of neighboring nodes and bonds linking these two nodes, being simple and understandable. By using this connection table, information on the chemical reaction can be stored in a recording medium without requiring so large capacity.

In the present invention, on the basis of only information on chemical substances such as the starting materials and the final product in the multi-step reaction there can be obtained systematic information on the multi-step reaction. Further, on the basis of only information on the starting materials at an arbitrary intermediate step in a series of chemical reactions composed of plural steps and products at subsequent steps, there can be obtained systematic information on an arbitrary intermediate reaction(s). Accordingly, multi-step reaction such as complicated synthesis reactions or arbitrary intermediate reactions thereof can be simply represented by the above-described structural diagram and/or connection table, and can be recorded, stored or displayed in the form of this representation mode.

In the structural diagram and the connection table, a series of chemical reactions can be basically described by a simple representation of nodes comprising atoms, groups, etc. and bonds linking two adjacent nodes. The bonds linking two nodes in the reaction system are distinguished and classified into the above-described three categories. Namely, bonds linking two nodes are represented in connection with the starting materials and the products, and hence, the structural diagram and the connection table contain information on a series of chemical reactions per se as well as substances concerned with said reactions on the whole. Accordingly, these registration modes according to the present invention is very superior to those of the conventional methods in that substance information as well as reaction information can be recorded and stored at the same time. By using the registered structural diagram and/or connection table, the retrieval and the collation of chemical reactions and substances can be made atom by atom for a series of chemical reactions (substances) or individual reactions (substances) at every arbitrary step.

By using the registration mode according to the present invention, information processing by computer is made easy and registration can be made without requiring so large storing capacity. The recording and storing of the multi-step reaction in a recording medium can be simply made, so that the storing and the management of information can be readily conducted.

When the connection table contains information on the space coordinate of each node, the structural diagram and the connection table can be transformed into each other, and a series of chemical reactions can be represented by any form.

In the second aspect of the present invention, when information on individual reactions is represented in the form of bond changes relating to the starting materials and products by denoting each bond linking two nodes with a pair of integers (a,b), wherein the integer a is bond multiplicity of the corresponding bond of the starting material and the integer b is difference in the bond multiplicity between the product and the starting material, a plurality of consecutive reactions can be also denoted simply in the similar manner by subjecting the inputted information to appropriate operational processing. Further, a series of chemical reactions can be represented in the form of structural diagram and/or connection table on the basis of the inputted information.

Accordingly, when information on various chemical reactions is registered in a computer in the form of a connection table by use of the pair of integers (a,b), multi-step reaction involving consecutive reactions can be simply represented by a similar mode. Thus, the storing and the management of information on complicated synthesis reactions and substances concerned with said reactions can be made much easier. At the same time, individual reactions and substances concerned therewith can be identified as unit reactions and intermediate products relating to the complicated synthesis reactions, so that the reaction information can be utilized more effectively.

Therefore, the information retrieval of chemical reactions and substances concerned therewith can be made effectively in a short time on the basis of information on multi-step reactions obtained directly from the starting materials and the products or obtained by subjecting information on individual reactions to operational processing, so that the time required for the collection of information on studies and investigations can be shortened, the amount of information can be increased and efficient researches can be achieved.

The multi-step reaction information obtained by the method of the present invention can be effectively applied to the fields of structural analysis of chemical substance, molecular modeling and heuristic analysis of organic synthesis, all of which are highly demanded by workers concerned with the manufacture of medicines. Further, retrieval of substructures of chemical substances and chemical reactions, correlation between structure and activity, design of synthetic pathways, automatic determination of the chemical structure of unknown compounds, mechanistic evaluation for the reaction of complicated compounds under certain conditions and prediction of mechanism therefor can be made within a practically possible range in a short time.

BRIEF DESCRIPTION OF THE DRAWING

Each of FIGS. 1 and 2 illustrates a flow chart for performing the method of the present invention.

DETAILED DESCRIPTION OF THE INVENTION

In the method for processing information on multi-step chemical reactions according to the present invention, in the first, structures of the starting materials in the j-th step reaction are topologically superposed upon those of the products in the k-th step reaction on the basis of the inputted information thereon; bonds are distinguished and classified into three categories of (1) bonds linking two nodes appearing only in the starting stage, (2) bonds linking two nodes appearing only in the product stage and (3) bonds linking two nodes appearing both in the starting and product stages; and there are/is then prepared a structural diagram (imaginary transition structure) and/or a connection table which represent changes in the structures of chemical substances during a series of chemical reactions from the j-th step through the k-th step.

In the description, n means the number of steps of the overall reaction, being a positive integer of 2 or greater, and j and k are each a positive integer satisfying the condition of $1 \leq j < k \leq n$.

Now, the method of the present invention will be described by referring to the Grignard reaction of ethyl acetate. The chemical reaction is a two-step reaction represented by the following equation:

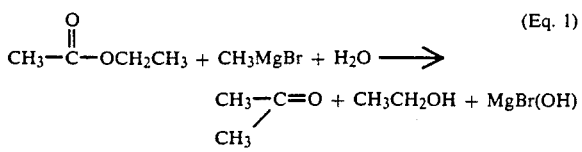
(Eq. 1)

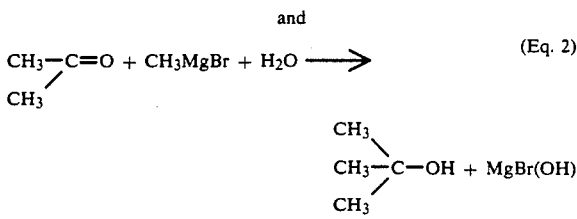
(Eq. 2)

All of the starting materials in the first step reaction (which constitute the starting stage) and all of the products in the second step reaction (which constitute the product stage) are represented by ordinary structural formulae, and nodes therefore are decided and consecutively numbered in correspondence between the starting stage and the product stage as follows.

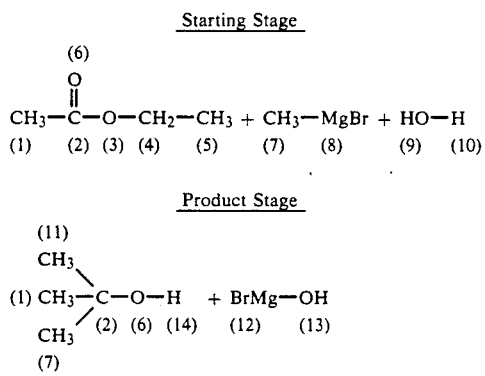

In the information processing according to the invention, the substance information on structures of the starting materials and the products can be input in the form of a figure which is easy to be treated by technologists such as the structural formula (two-dimensional form) or a three-dimensional form. The substance information may be input one by one in an interactive mode as character information, for example, "node (1) and node (2) are linked by a bond having a multiplicity of 1". In the case of the input by character, symbol, etc., the locational information such as two-dimensional or three-dimensional coordinates of nodes can be also input.

Based on these input information, the starting stage (starting material group) and the product stage (product group) are topologically superposed. The term "topologically superpose" used herein means that the chemical structures of the starting materials are combined with those of the products in such a manner that nodes appearing in the former coincide with those appearing in the latter. Thus, the following diagram is obtained:

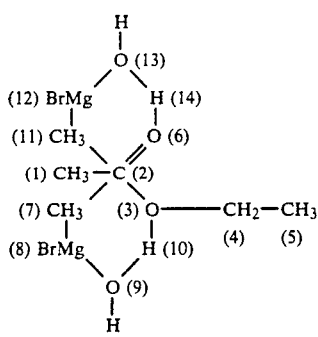

Subsequently, bonds appearing in the obtained diagram are distinguished and denoted as follows:
(i) bonds appearing both in the starting and product stage are denoted by the symbol —,
(ii) bonds appearing only in the starting stage are denoted by the symbol —, and
(iii) bonds appearing only in the product stage are denoted by the symbol . . . .

A structural diagram (ITS 1) is obtained.

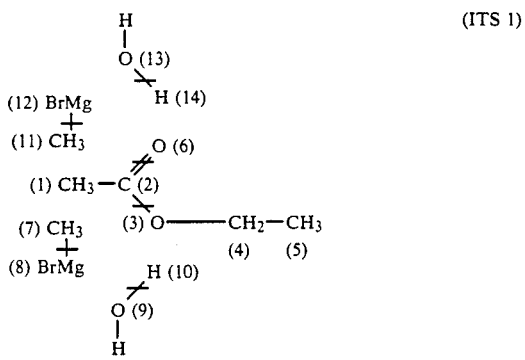

(ITS 1)

The obtained structural diagram is a two-dimensional diagram which represents structural changes of substances concerned with the two-step reaction in the integrated form and in the present invention, referred to as imaginary transition structure (abbreviated as ITS). Namely, the ITS is a diagram of two-dimension or three-dimension where bonds linking two adjacent nodes are distinguished between the starting materials and the products topologically superposed thereon and classified into said three categories (i) to (iii).

The above-described two-step reaction (represented by Eq. 1 and Eq. 2) can be summarized in the following equation:

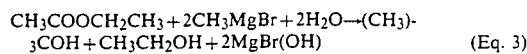

$$CH_3COOCH_2CH_3 + 2CH_3MgBr + 2H_2O \rightarrow (CH_3)_3COH + CH_3CH_2OH + 2MgBr(OH) \quad \text{(Eq. 3)}$$

Accordingly, the above ITS 1 should be said to represent an imaginary transition structure of Eq. 3.

It is possible to prepare an imaginary transition structure of three-dimension based on the information on three-dimensional structures of chemical substances as well as the above-shown imaginary transition structure of two-dimension. The input information has to contain information on relative space configuration of each node (two-dimensional or three-dimensional coordinate) for preparing ITS's.

In the present invention, nodes of the substances concerned with a chemical reaction are allowed to be individual atoms contained in the starting and product stages, or groups such as functional groups, for example, methyl group (node 5), methylene group (node 4), etc. Part of nodes appearing in the starting and product stages may be omitted in representing the chemical reaction, and the invention is not restricted by the way of decision of nodes.

In the imaginary transition structure (ITS) according to the invention, the notation for distinguishing the three kinds of bonds is by no means limited to the symbols defined by the above (i) to (iii), but the notation may be done by any means, for example: characters such as numerals (1, 2, 3, ...), colors (black, red, green, etc.), so long as users can judge the notation through the senses and it can be processed by computer.

In the invention hereinafter,
(i) bonds (symbol ——) appearing both in the starting and product stages are referred to as colorless bonds or "par-bonds",
(ii) bonds (symbol ——) appearing only in the starting stage are referred to as "out-bonds", and
(iii) bonds (symbol . . . ) appearing only in the product stage are referred to as "in-bonds".

Further, the out- and in-bonds are together referred to as colored bond and all the bonds appeared in ITS (par-, out- and in-bonds) are referred to as "ITS bonds" or imaginary bonds.

The types of bonds appearing in the imaginary transition structure are shown in Table 1, wherein the numerical value in the horizontal means a characteristic of in-and-out.

TABLE 1

| Characteristic of In-and-out | −3 | −2 | −1 | 0 | +1 | +2 | +3 |
|---|---|---|---|---|---|---|---|
| Single Bond | | | | ╪ (1 − 1) | —— (1 + 0) | ⋯ (0 + 1) | |
| Double Bond | | ╪╪ (2 − 2) | ╪— (2 − 1) | —— (2 + 0) | —— (1 + 1) | ⋯ (0 + 2) | |
| Triple Bond | ╪╪╪ (3 − 3) | ╪╪— (3 − 2) | ╪—— (3 − 1) | —— (3 + 0) | —— (2 + 1) | —— (1 + 2) | ⋯ (0 + 3) |

In Table 1, a bond represented by the symbol . . . is a single in-bond and denoted by a pair of integers (0+1) where 0 indicates that no bond is in the starting stage before reaction and +1 indicates that a bond is singly formed in the product stage after reaction. Similarly, a bond represented by the symbol —— is a single out-bond and denoted by a pair of integers (1-1), which means that a single bond in the starting stage before reaction is cleaved (to disappear) in the product stage after reaction. A bond represented by a pair of integers (2-1) is a double bond singly cleaved and denoted by the symbol .

In this way, the kinds of bonds can be denoted by a pair of integers (a,b) wherein the integer a is bond multiplicity of the corresponding bond of the starting material and the integer b is difference in the bond multiplicity between the product and the starting material, which is referred to as "complex bond number" or "imaginary multiplicity". Even when the bond multiplicity is two or more, it can be simply denoted. If desired, the comma (,) of (a,b) may be deleted. This notation does not need large storage capacity and can be directly processed by computer, so that the notation is particularly preferred in the storage of data on chemical reactions and suitably employed in preparing a connection table described below.

A plurality of consecutive reactions are entered (registered) in a computer in the form of the resulting two-dimensional or three-dimensional imaginary transition structure (diagram). This entry form is very excellent in that it is in a form similar to the structural formula or the three-dimensional form which can be visually acceptable and immediately understandable to chemists who intend to utilize information on chemical reaction.

In the processing method of the present invention, there can be also prepared a connection table of ITS (simply referred to as connection table) containing information on nodes, neighor nodes and bonds linking said two nodes on the basis of the input information on the starting materials and the products, to represent the information on chemical reactions with the connection table.

The structures of the starting materials are topologically superposed upon those of the products, and the bonds are distinguished and classified into the above three kinds of bonds, to prepare the imaginary transition structure (ITS 1). Then, based on the ITS, the nodes, the neighbor nodes, the bonds linking two nodes and if desired, the coordinates of nodes are represented by numeral, character, etc. to list up them.

ethanol and hydroxyl magnesium bromide) concerned with the reaction.

Alternatively, the connection table may be directly prepared from the input information, not preparing the imaginary transition structure. In this processing, "topologically superpose" means that the corresponding bonds are compared and collated between the structures of the starting materials and those of the products as well as that both the structures are graphically superposed in such a manner that the nodes are coincident with each other.

A plurality of consecutive reactions can be also entered in the form of the connection table in a computer. This entry form is superior in that it does not require large storage capacity and can be directly processed by the computer. It is possible to enter a combination of the connection table and the imaginary transition structure in the computer as a preferred embodiment of the present invention.

While the method of the present invention has been described above by referring to the two-step reaction wherein $j=1$ and $k=n=2$, the method of the present invention is not limited to two consecutive reactions, but can be applied to three or more consecutive reactions (three or more-step reactions). Accordingly, when $n>3$, arbitrary multi-step reaction can also be represented by the imaginary transition structure and/or connection table thereof, so long as j and k satisfy the condition of $1 \leq j < k \leq n$.

More in detail, when $j=1$ and $k=n$, the overall reaction is represented by ITS and/or connection table;

when $j=1$ and $k<n$, intermediate reactions from the 1-st step through the k-th step is represented by ITS and/or connection table; and when $j \geq 2$ and $k \leq n$, intermediate reactions from the j-th step through the k-th step is represented by ITS and/or connection table.

In this way, arbitrary consecutive reactions among multi-step reaction can be represented in the form of imaginary transition structure and/or connection table.

The information on the space coordinates of nodes may be incorporated in the connection table as described above. Further, information on stereochemistry

TABLE 2

| Node No. | Kind | Neighbor 1 Node (a,b) | Neighbor 2 Node (a,b) | Neighbor 3 Node (a,b) | Neighbor 4 Node (a,b) | Neighbor 5 Node (a,b) |
|---|---|---|---|---|---|---|
| 1 | $CH_3$ | 2 (1 + 0) | | | | |
| 2 | C | 1 (1 + 0) | 3 (1 − 1) | 6 (2 − 1) | 7 (0 + 1) | 11 (0 + 1) |
| 3 | O | 2 (1 − 1) | 4 (1 + 0) | | | |
| 4 | $CH_2$ | 3 (1 + 0) | 5 (1 + 0) | | | |
| 5 | $CH_3$ | 4 (1 + 0) | | | | |
| 6 | O | 2 (2 − 1) | 14 (0 + 1) | | | |
| 7 | $CH_3$ | 2 (0 + 1) | 8 (1 − 1) | | | |
| 8 | MgBr | 7 (1 − 1) | 9 (0 + 1) | | | |
| 9 | OH | 8 (0 + 1) | 10 (1 − 1) | | | |
| 10 | H | 3 (0 + 1) | 9 (1 − 1) | | | |
| 11 | $CH_3$ | 2 (0 + 1) | 12 (1 − 1) | | | |
| 12 | MgBr | 11 (1 − 1) | 13 (0 + 1) | | | |
| 13 | OH | 12 (0 + 1) | 14 (1 − 1) | | | |
| 14 | H | 6 (0 + 1) | 13 (1 − 1) | | | |

Table 2 shows the resulting connection table of the Grignard reaction. The connection table is a table in which all nodes, two-dimensional coordinates thereof (node 1 being the origin), all nodes neighboring on each node and the kinds of bonds linking two adjacent nodes are listed in order of node's number with respect to the starting stage (ethyl acetate, methyl magnesium bromide and water) and the product stage (tert-butanol, and electronic charges of nodes; information on spectral and physical properties of substances related to chemical reactions; and information on reaction enthalpy, reaction temperature, reaction time, catalysts, reaction atmosphere, reaction media, yields, by-products, etc. may be combined to the imaginary transition structure and/or the connection table, if desired. When the ITS's and/or connection tables stored in a computer contain these additional information, they can be widely used as data base in the fields of structure search systems, reaction search systems and design of organic synthesis pathways.

In entering the imaginary transition structures and/or connection tables may be numbered one by one or reaction names may be registered together with them in order to facilitate the storage, management and retrieval of the reaction information.

It is also possible to prepare the imaginary transition structure from the registered connection table, that is, the imaginary transition structures and the connection tables can be transformed into each other in the above-described various search systems. This arbitrary transformation brings about the enhancement in the all-around application of the search system and the usefullness thereof.

The entry of the imaginary transition structure and/or connection table in a computer may be done by storing them in main storage thereof or in an appropriate recording medium (magnetic disk, optical disk or magnetic tape). The registered ITS and/or connection table can be recorded on a recording material such as plain paper by an appropriate recording device, or can be displayed on a colored CRT connected to the computer or electronic equipment.

It is further possible to obtain the desired information by conducting various processing for the registered imaginary transition structures and/or connection tables thereof. For instance, when only in-bonds are deleted from the ITS and/or the connection table, that is the in-bonds are changed to non-bonds, there can be obtained the structures of the starting materials in the first step reaction (initial starting materials of the two-step reaction), while the structures of the products in the second step reaction (final products of the two-step reaction) can be obtained when only out-bonds are deleted therefrom. This means that the imaginary transition structures and/or the connection tables according to the present invention contain information not only on chemical reactions but also on chemical substances, and that it is possible to carry out the retrieval of chemical reactions as well as that of chemical compounds by the use of this entry mode.

When only colorless bonds are deleted from ITS 1, there can be obtained diagram (pattern) in which nodes are connected with alternative in-bonds and out-bonds: [(2)−(3)+(10)−(9)+(8)−(7)+(2) and (2)−(6)+(14)−(13)+(12)−(11)+(2)], wherein the signs − and + represent out-bond and in-bond, respectively. These are referred to as "reaction string". The reaction string(s) derived from ITS is inherent to a reaction type. The above reaction strings are diagrams inherent to the Grignard reaction. Namely, it is possible to independently extract a reaction string which is characteristic representation for every reaction type, whereby the retrieval of chemical reactions will become further easy. The above-described reaction is a two-step reaction and hence, it has two reaction strings. It is also possible to extract a ring structure (a bridge of ring opening, a bridge of ring closure, etc.) concerned with a chemical reaction.

Methods for further processing information on chemical reactions are described in our co-pending Japanese patent applications No. 60(1985)-185386 filed on Aug. 2, 1985; No. 60(1985)-197463 filed on Sept. 5, 1985; and No. 60(1985)-199920 filed on Sept. 9, 1985.

Accordingly, the imaginary transition structures and the connection tables can be utilized as the optimum entry forms in the various fields of chemistry to which the computer is applicable, i.e., the molecular modeling according to the specific properties of substances, the design of synthetic pathways of organic compounds and the determination of structures of unknown compounds.

In the second, in the method for processing information on multi-step reactions according to the present invention, information on each step reaction is represented by bond information wherein each bond linking two nodes for every reaction is denoted by a pair of integers $(a_x^i, b_x^i)$ [wherein i is a positive integer within a range of $1 \leq i \leq n$, n is a positive integer of 2 or greater, being the total number of steps of the overall reaction, the integer $a_x^i$ is bond multiplicity of the starting material of the bond x in the i-th step reaction, the integer $b_x^i$ is difference in the bond multiplicity of the bond x between the starting material and the product]; and said reaction information is subjected to appropriate operational processing to thereby denote information on consecutive reactions from the j-th step through the k-th step with a pair of integers $(a_x^{jk}, b_x^{jk})$ [wherein j and k are each a positive integer satisfying the condition of $1 \leq j < k \leq n$].

When further appropriate processing is conducted for information on the multi-step reaction represented by the pair of integers $(a_x^{jk}, b_x^{jk})$, the multi-step reaction can be represented in the form of imaginary transition structure and/or connection table.

Now, the method of the present invention will be described by referring to the above-described Grignard reaction of ethyl acetate. This reaction is a two-step reaction represented by Eqs. 1 and 2. The imaginary transition structures at individual steps can be represented as follows.

Imaginary transition structure of Eq. 1:

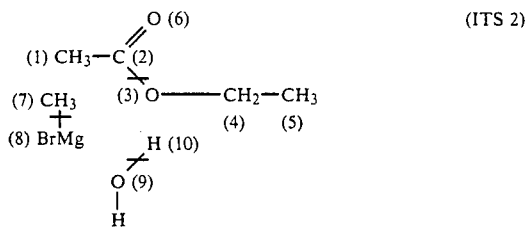

(ITS 2)

Imaginary transition structure of Eq. 2:

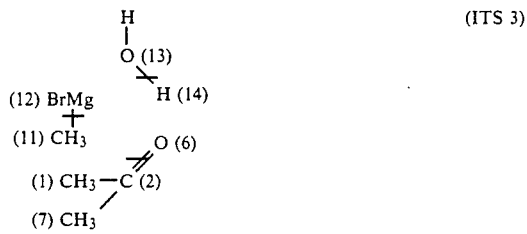

(ITS 3)

The connection tables at individual steps are respectively shown in Tables 3 and 4.

As shown in the connection tables of Tables 3 and 4, the reaction information for each step is denoted by a pair of integers $(a_x^1, b_x^1)$ or $(a_x^2, b_x^2)$ for each bond linking two nodes.

TABLE 3

| Node No. | Kind | Neighbor 1 Node (a,b) | Neighbor 2 Node (a,b) | Neighbor 3 Node (a,b) | Neighbor 4 Node (a,b) | Neighbor 5 Node (a,b) |
|---|---|---|---|---|---|---|
| 1 | CH$_3$ | 2 (1 + 0) | | | | |
| 2 | C | 1 (1 + 0) | 3 (1 − 1) | 6 (2 + 0) | 7 (0 + 1) | |
| 3 | O | 2 (1 − 1) | 4 (1 + 0) | | | |
| 4 | CH$_2$ | 3 (1 + 0) | 5 (1 + 0) | | | |
| 5 | CH$_3$ | 4 (1 + 0) | | | | |
| 6 | O | 2 (2 + 0) | | | | |
| 7 | CH$_3$ | 2 (0 + 1) | 8 (1 − 1) | | | |
| 8 | MgBr | 7 (1 − 1) | 9 (0 + 1) | | | |
| 9 | OH | 8 (0 + 1) | 10 (1 − 1) | | | |
| 10 | H | 3 (0 + 1) | 9 (1 − 1) | | | |

TABLE 4

| Node No. | Kind | Neighbor 1 Node (a,b) | Neighbor 2 Node (a,b) | Neighbor 3 Node (a,b) | Neighbor 4 Node (a,b) | Neighbor 5 Node (a,b) |
|---|---|---|---|---|---|---|
| 1 | CH$_3$ | 2 (1 + 0) | | | | |
| 2 | C | 1 (1 + 0) | 6 (2 − 1) | 7 (1 + 0) | 11 (0 + 1) | |
| 6 | O | 2 (2 − 1) | 14 (1 − 1) | | | |
| 7 | CH$_3$ | 2 (1 + 0) | | | | |
| 11 | CH$_3$ | 2 (0 + 1) | 12 (1 − 1) | | | |
| 12 | MgBr | 11 (1 − 1) | 13 (0 + 1) | | | |
| 13 | OH | 12 (0 + 1) | 14 (1 − 1) | | | |
| 14 | H | 6 (0 + 1) | 13 (1 − 1) | | | |

The operations for bond of:

$$a_x^{12} = a_x^1$$

$$b_x^{12} = b_x^1 + b_x^2$$

are made on all bonds linking two nodes. Subsequently, each bond is denoted by a pair of integers $(a_x^{12}, b_x^{12})$.

For instance, the bond operation on the bond linking nodes (2) and (6) is expressed as follows:

$$(2+0)+(2-1)=(2-1)$$

In this case, the following relation holds.

$$a_x^1 + b_x^1 = a_x^2$$

Thus, information on said two-step reaction can be obtained as bond information in the form of a set of $(a_x^{12}, b_x^{12})$ wherein x takes every bond. Consequently, there can be obtained information corresponding to the connection table of Table 2.

Further, the imaginary transition structure (ITS 1) of the two-step reaction is obtained by distinguishing bonds linking two nodes between colorless bond, out-bond and in-bond according to the obtained bond information and connecting the nodes.

The above-described principles can be applied to multi-step reaction composed of n steps, since three or more-step reaction is considered to be continuation of the two-step reaction.

Suppose that a given bond linking two nodes is changed in turn at each step of the multi-step reaction composed of n steps as follows:

$$(a^1,b^1), (a^2,b^2), \ldots (a^i,b^i), \ldots (a^n,b^n)$$

When the bond in the reactions from the j-th step through the k-th step (wherein j and k are each a positive integer satisfying the condition of $1 \leq j < k \leq n$) is represented by:

$$(a^j,b^j)+(a^{j+1},b^{j+1})+\ldots$$
$$+(a^{k-1},b^{k-1})+(a^k,b^k)=(a^{jk},b^{jk})$$

the following expression holds:

$$a^{jk} = a^j$$

$$b^{jk} = b^j + b^{j+1} + \ldots + b^{k-1} + b^k \quad \text{(Expression 1)}$$

The following expression holds for the bond $(a^i,b^i)$ at an arbitrary step:

$$a^{i-1} + b^{i-1} = b^i \quad \text{(Expression 2)}$$

Expression 1 is called "bond operation" for the determination of a bond $(a^{jk},b^{jk})$ in the consecutive reactions from the j-step through the k-step. Expression 2 is called condition for said consecutive reactions.

In other words, when Expression 2 applies to all bonds appearing in ITS of the (i−1)th step reaction and in ITS of the i−th step reaction, ITS (i−1) and ITS (i) can be considered to be consecutive reactions. The confirmation of the results on the bond $(a^{jk},b^{jk})$ can be also performed by verifying every step of the j-th to the k-th steps by using Expression 2.

Particularly, when j=1 and k=n, bond information $(a_x,b_x)$ for the overall reaction is obtained;

when j=1 and k<n, bond information $(a_x^{1k},b_x^{1k})$ for intermediate reactions from the 1-st step through the k-th step is obtained; and when $j \geq 2$ and $k \leq 2$, bond information $(a_x^{jk},b_x^{jk})$ for intermediate reactions from the j-th step through the k-th step is obtained.

In this way, information on arbitrary consecutive reactions among the multi-step reaction can be obtained in the form of a set of $(a_x^{jk},b_x^{jk})$ notation, imaginary transition structure and/or connection table.

Through the above n-step reaction, it is preferred to give common numbers to nodes concerned with the reaction. For instance, node's numbers used in the i-th step reaction may be commonly used in other step reactions.

Further, ITS (ITS 2) of the first step reaction is obtained from the ITS (ITS 1) of the two-step Grignard reaction by deleting the in-bonds (the symbol ...) in the second step reaction from ITS 1 to change them to non-bonds, changing the out-bonds (the symbol ——) in the second step reaction to colorless bonds (the symbol ———) and deleting nodes which are not connected with the remaining reaction string (which is a group comprises nodes connected with alternate out-bonds and in-bonds) from ITS 1.

In general, ITS of the (n-1)-step reactions can be obtained from an imaginary transition structure of multi-step reaction composed of n steps by deleting in-bonds in the final step reaction from the ITS of the multi-step reaction to change them to non-bonds, changing out-bonds in the final step reaction to colorless bonds and deleting nodes which are not connected with the remaining reaction string therefrom.

This operation of restoring ITS of the multi-step reaction to ITS of one step back is referred to as "projection to the intermediate stage" (abbreviated by PI).

When consecutive multi-step reaction are recorded and stored as reaction route, a synthesis space is prepared and ITS of each step reaction is then prepared on the basis of the synthesis space. ITS's of arbitrary intermediate reactions are further prepared according to the method of the present invention and a set of the prepared ITS's (referred to as reaction-route class) is registered.

For instance, a synthesis space in the Grignard reaction is obtained by listing all nodes appearing in Eqs. 1 and 2 and affording a set of nodes. Thus, the synthesis space contains all nodes appearing in the synthetic pathway. The nodes may be numbered, if desired.

Synthesis space

```
                  H
                  |
                  O (13)
    (12) BrMg         H (14)
    (11) CH3          O (6)
    (1) CH3           C (2)
    (7) CH3           O   CH2   CH3
                     (3)  (4)   (5)
    (8) BrMg          H (10)
                      O (9)
                      |
                      H
```

Within this synthesis space, the ITS's (ITS 2 and ITS 3) of the individual step reactions are represented as follows:

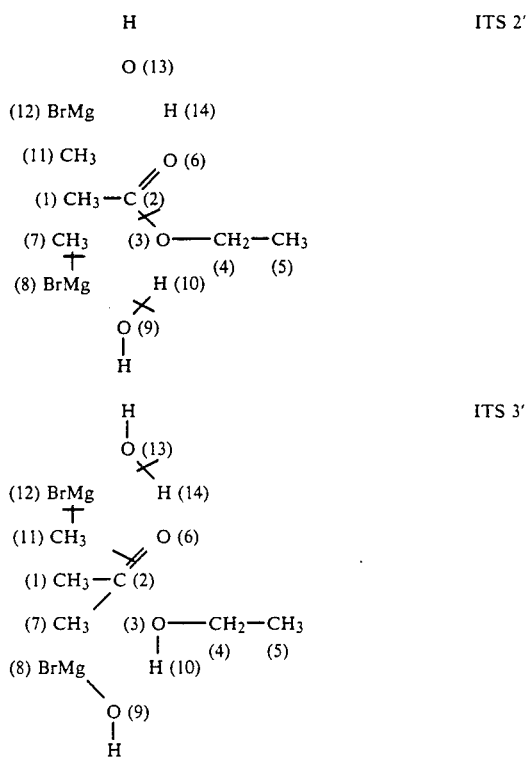

ITS in a combination of these ITS 2' and ITS 3', that is, ITS of the two-step reaction is obtained as ITS 1 by performing the aforementioned bond operation.

The three set of ITS's obtained are referred to as "reaction-route classes".

It is preferred to prepare reaction-route classes for connection tables in a similar manner to that described above.

Further, the method of the present invention will be described by referring to consecutive reactions composed of the following five steps:

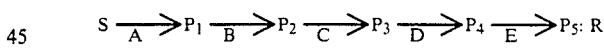

wherein R means a synthesis space of the five-step reaction, S represents the starting materials of the five-step reaction and $P_1$ to $P_5$ represent the products in the individual step reactions, respectively.

When ITS at each step is represented by A, B, C, ..., reaction-route classes of the five-step reaction are filed as shown in Table 5.

TABLE 5

| Step | ITS | | | |
|---|---|---|---|---|
| 5 | EDCBA | DCBA | CBA | BA | A |
| 4 | EDCB | DCB | CB | B | |
| 3 | EDC | DC | C | | |
| 2 | ED | D | | | |
| 1 | E | | | | |

In the file of reaction-route classes shown in Table 5, all ITS's which are positioned on the right side of a given ITS and under said a given ITS represent the partial (intermediate) reactions of said a given ITS. For instance, when DCB is a given ITS, ITS's representing the partial reactions thereof are CB, B, DC, C and D.

The retrieval of chemical reactions can be made by utilizing the file of reaction-route classes. When ITS (DCB) is found out (hit), the file is opened to output all the reactions related to DCB. It is desirable to make processing for dividing DCB into individual reactions (unit reactions) by using the above PI operation (PI module).

Accordingly, imaginary transition structure and/or connection table of every intermediate reaction (partial reaction) contained in a series of reactions (reaction route) can be prepared on the basis of the inputted information on individual reactions by the above-described direct method or processing method of bond operation to form a reaction route. Further, the imaginary transition structures and/or the connection tables prepared as the reaction route can be registered, recorded or displayed through an appropriate means. In this way, the individual reactions and the arbitrary intermediate reactions can be positioned and identified within the reaction route. The registered reaction route can be used in various fields of the reaction retrieval, the retrieval of the structures of substances, the design of organic synthesis and the molecular modeling.

The following examples will further illustrate the method for processing information on chemical reactions according to the present invention.

EXAMPLE 1

Methylation Reaction of Cycloheptanone

The reaction is a series of reactions from step [A] to step [C] represented by the schematic equation.

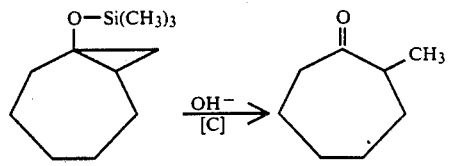

(1) An imaginary transition structure (ITS 4) of the two-step reaction composed of steps [A] and [B] was prepared, on the basis of the structural formula of the starting material in the [A]-step reaction and that of the product in the [B]-step reaction.

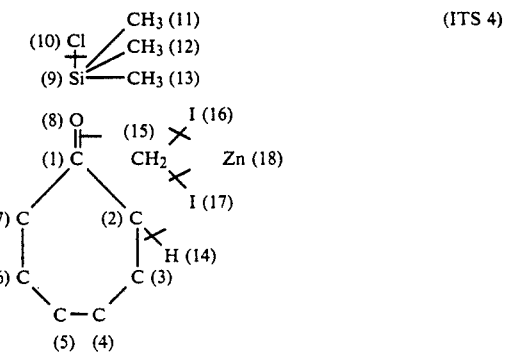

A connection table corresponding to ITS 4 was prepared. The connection table is set forth in Table 6, which includes information on the two-dimensional coordinate (xy-coordinate) of each node.

TABLE 6

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 0) | 7 (1 + 0) | 8 (2 − 1) | 15 (0 + 1) | |
| 2 | C | 173 | 100 | 1 (1 + 0) | 3 (1 + 0) | 14 (1 − 1) | 15 (0 + 1) | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 − 1) | 9 (0 + 1) | | | |
| 9 | Si | 0 | 600 | 8 (0 + 1) | 10 (1 − 1) | 11 (1 + 0) | 12 (1 + 0) | 13 (1 + 0) |
| 10 | Cl | 0 | 800 | 9 (1 − 1) | | | | |
| 11 | CH3 | 100 | 773 | 9 (1 + 0) | | | | |
| 12 | CH3 | 173 | 700 | 9 (1 + 0) | | | | |
| 13 | CH3 | 200 | 600 | 9 (1 + 0) | | | | |
| 14 | H | 314 | −41 | 2 (1 − 1) | | | | |
| 15 | CH2 | 200 | 200 | 1 (0 + 1) | 2 (0 + 1) | 16 (1 − 1) | 17 (1 − 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |

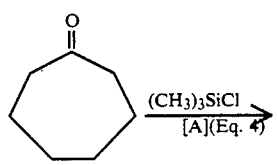

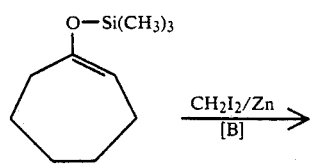

(2) A series of reactions composed of steps [A] to [C] have the following synthesis space.

Synthesis space

(10) Cl   CH3 (11)

CH3 (12)

OH   Si   CH3 (13)
(20)  (9)

(8) O   H (19)

-continued
Synthesis space

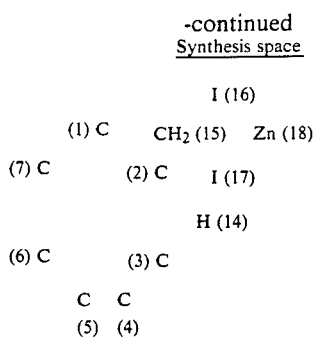

Imaginary transition structures at the individual steps are respectively denoted in the synthesis space as follows:

ITS at step [A]

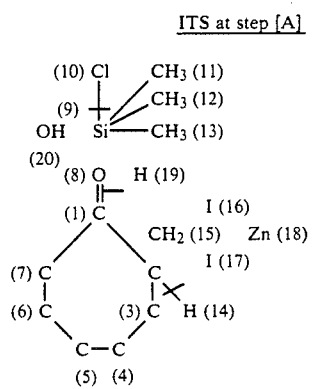

(ITS 5)

-continued
ITS at step [B]

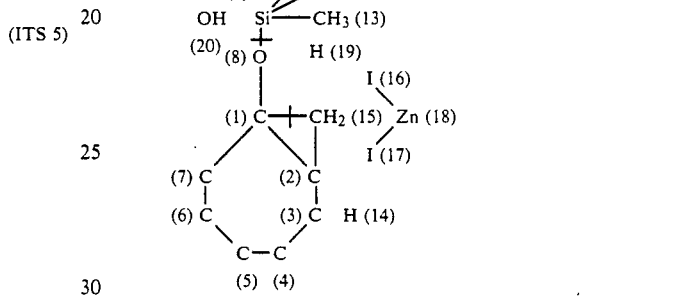

(ITS 6)

ITS at step [C]

(ITS 7)

Connection tables at steps [A], [B] and [C] are respectively set forth in Tables 7 to 9.

TABLE 7

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 1) | 7 (1 + 0) | 8 (2 − 1) | | |
| 2 | C | 173 | 100 | 1 (1 + 1) | 3 (1 + 0) | 14 (1 − 1) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 − 1) | 9 (0 + 1) | | | |
| 9 | Si | 0 | 600 | 8 (0 + 1) | 10 (1 − 1) | 11 (1 + 0) | 12 (1 + 0) | 13 (1 + 0) |
| 10 | Cl | 0 | 800 | 9 (1 − 1) | | | | |
| 11 | CH₃ | 100 | 773 | 9 (1 + 0) | | | | |
| 12 | CH₃ | 173 | 700 | 9 (1 + 0) | | | | |
| 13 | CH₃ | 200 | 600 | 9 (1 + 0) | | | | |
| 14 | H | 314 | −41 | 2 (1 − 1) | | | | |

TABLE 8

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (2 − 1) | 7 (1 + 0) | 8 (1 + 0) | 15 (0 + 1) | |
| 2 | C | 173 | 100 | 1 (2 − 1) | 3 (1 + 0) | 15 (0 + 1) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 + 0) | | | |
| 9 | Si | 0 | 600 | 8 (1 + 0) | 11 (1 + 0) | 12 (1 + 0) | 13 (1 + 0) | |
| 10 | Cl | 0 | 800 | | | | | |
| 11 | CH₃ | 100 | 773 | 9 (1 + 0) | | | | |
| 12 | CH₃ | 173 | 700 | 9 (1 + 0) | | | | |
| 13 | CH₃ | 200 | 600 | 9 (1 + 0) | | | | |
| 14 | H | 314 | −41 | | | | | |
| 15 | CH₂ | 200 | 200 | 1 (0 + 1) | 2 (0 + 1) | 16 (1 − 1) | 17 (1 − 1) | |
| 16 | I | 373 | 300 | 15 (1 − 1) | 18 (0 + 1) | | | |
| 17 | I | 373 | 100 | 15 (1 − 1) | 18 (0 + 1) | | | |

TABLE 8-continued

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 18 | Zn | 546 | 200 | 16 (0 + 1) | 17 (0 + 1) | | | |

TABLE 9

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 0) | 7 (1 + 0) | 8 (1 + 1) | 15 (1 − 1) | |
| 2 | C | 173 | 100 | 1 (1 + 0) | 3 (1 + 0) | 15 (1 + 0) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 − 1) | | | |
| 9 | Si | 0 | 600 | 8 (1 − 1) | 11 (1 + 0) | 12 (1 + 0) | 13 (1 + 0) | 20 (0 + 1) |
| 10 | Cl | 0 | 800 | | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | | | | | |
| 15 | CH$_2$ | 200 | 200 | 1 (1 − 1) | 2 (1 + 0) | 19 (0 + 1) | | |
| 16 | I | 373 | 300 | 18 (1 + 0) | | | | |
| 17 | I | 373 | 100 | 18 (1 + 0) | | | | |
| 18 | Zn | 546 | 200 | 16 (1 + 0) | 17 (1 + 0) | | | |
| 19 | H | 200 | 400 | 15 (0 + 1) | | | | |
| 20 | OH | −200 | 600 | 9 (0 + 1) | | | | |

The bond operation was performed on all set of ($a_x^i$, $b_x^i$) denoted in the connection tables to make the three-step reaction composed of steps [A] to [C] summarized and represented by (a,b).

For example, the bond operation was performed on the bond linking nodes (1) and (2) as follows:

$$(1+1)+(2-1)+(1+0)=(1+0)$$

The results are set forth in Table 10.

An imaginary transition structure of the three-step reaction composed of steps [A] to [C] was prepared on the basis of the connection table shown in Table 10.

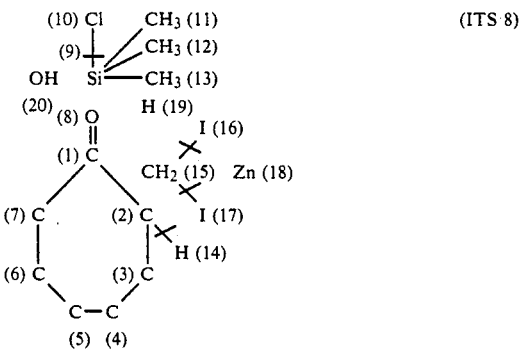

(ITS 8)

TABLE 10

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a,b) | Node (a,b) | Node (a,b) | Node (a,b) | Node (a,b) |
| 1 | C | 0 | 200 | 2 (1 + 0) | 7 (1 + 0) | 8 (2 + 0) | | |
| 2 | C | 173 | 100 | 1 (1 + 0) | 3 (1 + 0) | 14 (1 − 1) | 15 (0 + 1) | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (2 + 0) | | | | |
| 9 | Si | 0 | 600 | 10 (1 − 1) | 11 (1 + 0) | 12 (1 + 0) | 13 (1 + 0) | 20 (0 + 1) |
| 10 | Cl | 0 | 800 | 9 (1 − 1) | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | 2 (1 − 1) | | | | |
| 15 | CH$_2$ | 200 | 200 | 2 (0 + 1) | 16 (1 − 1) | 17 (1 − 1) | 19 (0 + 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |
| 19 | H | 200 | 400 | 15 (0 + 1) | | | | |
| 20 | OH | −200 | 600 | 9 (0 + 1) | | | | |

I claim:

1. A method for processing information on a two or more-step chemical reaction wherein individual reactions of producing at least one product from at least one starting material take place consecutively, to record and store said information in a computer system, which comprises:

- topologically superposing structure of the starting material in the j-th step reaction upon that of the product in the k-th step reaction on the basis of information on the structures of the starting material and the product, wherein j and k are each a positive integer satisfying the condition of $1 \leq j < k \leq n$ and n is a positive integer of 2 or greater, being the total number of steps of the overall reaction;
- distinguishing and classifying bonds into three categories of (1) bonds linking two nodes appearing both in the starting and product stages, (2) bonds linking two nodes appearing only in the starting stage and (3) bonds linking two nodes only in the product stage;
- preparing a structural diagram showing structural change of substances in the consecutive reactions of from the j-th step to the k-th step; and
- storing the prepared connection table in recording material.

2. The method for processing information on a two or more-step chemical reaction as claimed in claim 1, wherein said bonds linking two nodes in the structural diagram are distinguished and denoted by characters, symbols, colors or a combination thereof.

3. A method for processing information on a two or more-step chemical reaction wherein individual reactions of producing at least one product from at least one starting material take place consecutively, to record and store said information in a computer system, which comprises:

- topologically superposing structure of the starting material in the j-th step reaction upon that of the product in the k-th step reaction on the basis of information on the structures of the starting material and the product, wherein j and k are each a positive integer satisfying the condition of $1 \leq j < k \leq n$ and n is a positive integer of 2 or greater, being the total number of steps of the overall reaction;
- distinguishing and classifying bonds into three categories of (1) bonds linking two nodes appearing both in the starting and product stages, (2) bonds linking two nodes appearing only in the starting stage and (3) bonds linking two nodes only in the product stage; and
- preparing a connection table containing information on nodes, neighboring nodes and bonds linking said two nodes with respect to the consecutive reactions of from the j-th step to the k-th step; and
- storing the prepared connection table in recording material.

4. The method for processing information on a two or more-step chemical reaction as claimed in claim 3, wherein the bonds linking two nodes in said connection table are distinguished and denoted by a pair of integers $(a_x^{jk}, b_x^{jk})$, wherein j and k are each a positive integer satisfying the condition of $1 \leq j \leq k \leq n$, n is a positive integer of 2 or greater, being the total number of steps of the overall reaction, the integer $a_x^{jk}$ is bond multiplicity of the bond x of the starting material in the consecutive reactions of from the j-th step to the k-th step and the integer $b_x^{jk}$ is difference in the bond multiplicity of the bond x between the product and the starting material in said consecutive reactions.

* * * * *